(12) United States Patent
Howard et al.

(10) Patent No.: US 11,806,000 B2
(45) Date of Patent: Nov. 7, 2023

(54) TRANSSEPTAL SYSTEMS AND METHODS

(71) Applicant: MEDTRONIC, INC., Minnepolis, MN (US)

(72) Inventors: Stephen A. Howard, Forest Lake, MN (US); Kevin A. Knutsen, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 132 days.

(21) Appl. No.: 17/554,576

(22) Filed: Dec. 17, 2021

(65) Prior Publication Data
US 2022/0257226 A1 Aug. 18, 2022

Related U.S. Application Data

(60) Provisional application No. 63/149,468, filed on Feb. 15, 2021.

(51) Int. Cl.
*A61B 17/00* (2006.01)
*A61M 29/00* (2006.01)
(Continued)

(52) U.S. Cl.
CPC .... *A61B 17/00234* (2013.01); *A61B 17/3478* (2013.01); *A61M 25/09* (2013.01);
(Continued)

(58) Field of Classification Search
CPC .......... A61B 17/00234; A61B 17/3403; A61B 17/3421; A61B 17/3478;
(Continued)

(56) References Cited

U.S. PATENT DOCUMENTS

| 5,203,338 A | * | 4/1993 | Jang | A61M 25/0029 |
| | | | | 600/463 |
| 5,620,417 A | * | 4/1997 | Jang | A61F 2/958 |
| | | | | 604/158 |

(Continued)

FOREIGN PATENT DOCUMENTS

WO 9848882 11/1998

OTHER PUBLICATIONS

International Search Report and Written Opinion for related International Application No. PCT/US2022/016276 dated May 11, 2022 (13 pgs.).

*Primary Examiner* — Ryan J. Severson
(74) *Attorney, Agent, or Firm* — Michael Best & Friedrich LLP

(57) ABSTRACT

A transseptal system includes a needle, a guidewire, a handle, and a dilator. The handle defines a needle passage to slidably receive the needle, and a guidewire passage to slidably receive the guidewire. The dilator defines a lumen having a distal region and a proximal region. The dilator is coupled to the handle such that the lumen is open to the needle passage and the guidewire passage. The proximal region of the lumen is sized to simultaneously receive the needle body and the guidewire. The distal region is sized to slidably receive one of the needle and the guidewire on an individual basis. A transseptal puncture and access procedure can be performed, including puncturing tissue with the needle followed by immediate advancement of the guidewire into the accessed area, eliminating the need for multiple instrument exchanges during the procedure.

20 Claims, 16 Drawing Sheets

(51) Int. Cl.
*A61M 25/09* (2006.01)
*A61B 17/34* (2006.01)

(52) U.S. Cl.
CPC ... *A61M 29/00* (2013.01); *A61B 2017/00247* (2013.01); *A61B 2017/3405* (2013.01)

(58) Field of Classification Search
CPC .. A61B 2017/00247; A61B 2017/3405; A61B 2017/3445; A61B 2017/3449; A61M 25/09; A61M 29/00
See application file for complete search history.

(56) References Cited

U.S. PATENT DOCUMENTS

| | | | |
|---|---|---|---|
| 5,935,114 A | 8/1999 | Jang et al. | |
| 5,976,093 A * | 11/1999 | Jang | A61M 25/0068 600/585 |
| 5,997,523 A | 12/1999 | Jang | |
| 6,234,971 B1 * | 5/2001 | Jang | A61M 25/0068 600/585 |
| 6,730,037 B2 * | 5/2004 | Jang | A61B 17/22 600/585 |
| 7,963,947 B2 * | 6/2011 | Kurth | A61B 17/3478 604/164.08 |
| 9,149,602 B2 * | 10/2015 | Chow | A61M 25/003 |
| 9,950,144 B2 * | 4/2018 | Chow | A61M 25/003 |
| 11,103,276 B2 * | 8/2021 | Sarabia | A61B 17/0057 |
| 11,224,725 B2 * | 1/2022 | Pedersen | A61B 17/3468 |
| 11,426,565 B2 * | 8/2022 | Thomspon Smith | A61M 29/00 |
| 2003/0036729 A1 * | 2/2003 | Jang | A61B 17/22 604/174 |
| 2006/0253088 A1 * | 11/2006 | Chow | A61M 25/003 604/284 |
| 2007/0270741 A1 | 11/2007 | Hassett et al. | |
| 2009/0182281 A1 | 7/2009 | Kurth et al. | |
| 2012/0239069 A1 * | 9/2012 | Benscoter | A61B 17/3478 606/185 |
| 2016/0008578 A1 | 1/2016 | Chow et al. | |
| 2017/0065297 A1 | 3/2017 | Hareland | |
| 2018/0116690 A1 | 5/2018 | Sarabia et al. | |
| 2019/0015644 A1 | 1/2019 | Thomspon Smith et al. | |
| 2019/0167305 A1 | 6/2019 | Pedersen et al. | |
| 2020/0229805 A1 | 7/2020 | Gammie et al. | |
| 2020/0289796 A1 | 9/2020 | Kurth et al. | |
| 2022/0257226 A1 * | 8/2022 | Howard | A61M 25/09 |

* cited by examiner

TRANSSEPTAL SYSTEMS AND METHODS

CROSS-REFERENCE TO RELATED APPLICATIONS

This Non-Provisional Patent application claims the benefit of the filing date of U.S. Provisional Patent Application Ser. No. 63/149,468, filed Feb. 15, 2021, the entire teachings of which are incorporated herein by reference.

FIELD

The present disclosure relates to transseptal systems and methods. More particularly, it relates to systems and methods for performing an intracardiac transseptal puncture and access procedures, such as to puncture the atrial septum to gain access to the left atrium.

BACKGROUND

Many cardiac treatment procedures require access to the left atrium of the heart. For intravenous access, transseptal puncture is a critical step in gaining access to the left side of the heart. Typically, a clinician uses a sheath, dilator, puncturing or transseptal needle, and a guidewire. During a transseptal puncture/access procedure, the dilator is housed within the sheath, advanced into the superior vena cava (SVC) (or at least higher than the septal access point), then the guidewire is removed and is replaced by the transseptal needle, keeping care not to damage any atrial or venous structure. The needle, dilator, and sheath are then collectively retracted (which brings the tip of the dilator from the SVC into the right atrium and to the desired access point on the atrial septum, typically at the fossa ovalis). With the tip of the transseptal needle within the dilator, the sheath and/or the dilator is slowly and iteratively advanced, pushing against, and creating "tenting" within, the septum. The transseptal needle is then advanced to penetrate or puncture the atrial septum. Subsequently, the dilator and sheath will be advanced through the so-created puncture opening and into the left atrium, enlarging the septal opening and providing access to the left atrium. With some techniques, a guide wire is employed to better ensure that the dilator safely crosses into the left atrium and/or is safely located within the left atrium. For example, after puncturing the atrial septum, only a small portion of the dilator is advanced into the left atrium then the transseptal needle is removed, replaced with a guidewire. The guidewire is advanced into the left atrium and optionally anchored or placed to mitigate inadvertent damage to the cardiac tissues or structures (e.g., being placed within one of the left pulmonary veins). The guidewire can thus stabilize forward advancement of both the dilator and the sheath. As a point of reference, in some instances the tip of dilator may "jump" forward and perforate an adjacent structure, such as the left atrial free wall. Using a guidewire to help pass the dilator and sheath across the intra-atrial septum thus makes advancing the dilator safer.

The transseptal puncture systems and methods described above are well-accepted. While the use of guidewires is beneficial with transseptal puncture procedures, various time-consuming device exchanges are typically required.

SUMMARY

The inventors of the present disclosure have recognized a need to address one or more of the above-mentioned problems. The details of one or more aspects of the disclosure are set forth in the accompanying drawings and the description below. Other features, objects, and advantages of the techniques described in this disclosure will be apparent from the description and drawings, and from the claims.

Some aspects of the present disclosure relate to a transseptal system. The transseptal system includes a needle body, a guidewire, a handle, and a dilator body. The needle body defines a distal tip and an intermediate section proximal the distal tip. The guidewire defines a leading end and an intermediate segment proximal the leading end. The handle defines a needle passage and a guidewire passage. The needle passage is sized to slidably receive the intermediate section of the needle body, and the guidewire passage is sized to slidably receive the intermediate segment of the guidewire. The dilator body defines a distal end, a proximal end, and a lumen having a distal region open to the distal end and a proximal region open to the proximal end. The proximal end of the dilator body is coupled to the handle such that the lumen is open to the needle passage and the guidewire passage. The proximal region of the lumen is sized to simultaneously receive the intermediate section of the needle body and the intermediate segment of the guidewire. Further, the distal region of the lumen is sized to slidably receive the intermediate section of the needle body and the intermediate segment of the guidewire on an individual basis. With this construction, a transseptal puncture and access procedure can be performed, including puncturing tissue with the needle body followed by immediate advancement of the guidewire into the accessed area, eliminating the need for multiple instrument exchanges during the procedure. The distal segment of the dilator lumen is sized to disallow the advancement of both the guidewire and the needle simultaneously, thereby reducing risk of inadvertent/unintended puncture or damage. In some embodiments, the handle is provided as part of a handle assembly further including an actuator device connected to the handle and configured to retain the needle body. In some related embodiments, the actuator device is slidably connected to the handle. In some related embodiments, the handle and the actuator mechanism define a complementary engagement arrangement configured to selectively secure the actuator mechanism body relative to the handle in the rearward position. In some related embodiments, the handle assembly further includes a safety tab removably connected to the handle and arranged to prevent the actuator mechanism from being directed to a forward position.

Other aspects of the present disclosure related to a transseptal system. The transseptal system includes a handle assembly, a dilator body, and a needle body. The handle assembly includes a handle defining a needle passage and a guidewire passage. The dilator body defines a longitudinal axis, distal end, a proximal end, and a lumen having a distal region open to the distal end and a proximal region open to the proximal end. In this regard, a cross-sectional maximum outer dimension of the distal region of the lumen in a plane perpendicular to the longitudinal axis is less than a cross-sectional maximum outer dimension of the proximal region of the lumen in a plane perpendicular to the longitudinal axis. The proximal end of the dilator body is coupled to the handle such that the lumen is open to the needle passage and the guidewire passage. The needle body is coupled to the handle assembly and slidably received within the needle passage and the lumen. In some embodiments, the system further includes a guidewire configured to be slidably received within the guidewire passage and the lumen. In some embodiments, the needle body is formed of metal or other electrically conductive material that can optionally allow for electrical ablation (e.g., via RF energy applied by the needle body) to effect, or assisting in effecting, a tissue puncture.

Other aspects of the present disclosure relate to a method of creating a transseptal passage. The method includes advancing a dilator body over a guidewire to bring a distal end of the dilator body into contact with a first side of an atrial septum, the guidewire being slidably received within a lumen of the dilator body. The guidewire is retracted relative to the dilator body such that a leading end of the guidewire is located within the lumen. A hole is formed through the septum with a needle body while the leading end of the guidewire is maintained within lumen. In this regard, the needle body is advanced along the lumen to cause a distal tip of the needle body to extend from the distal end of the dilator body and puncture through the first side of the atrial septum to an opposing, second side of the atrial septum. The needle body is retraced relative to the dilator body following the step of forming a hole such that the distal tip of the needle body is located within the lumen. The guidewire is then advanced relative to the dilator body such that the leading end of the guidewire extends distally beyond the distal end of the dilator body and the second side of the atrial septum. In some embodiments, the step of advancing the guidewire includes directing the leading end into a left atrium.

DETAILED DESCRIPTION

Figure 1:
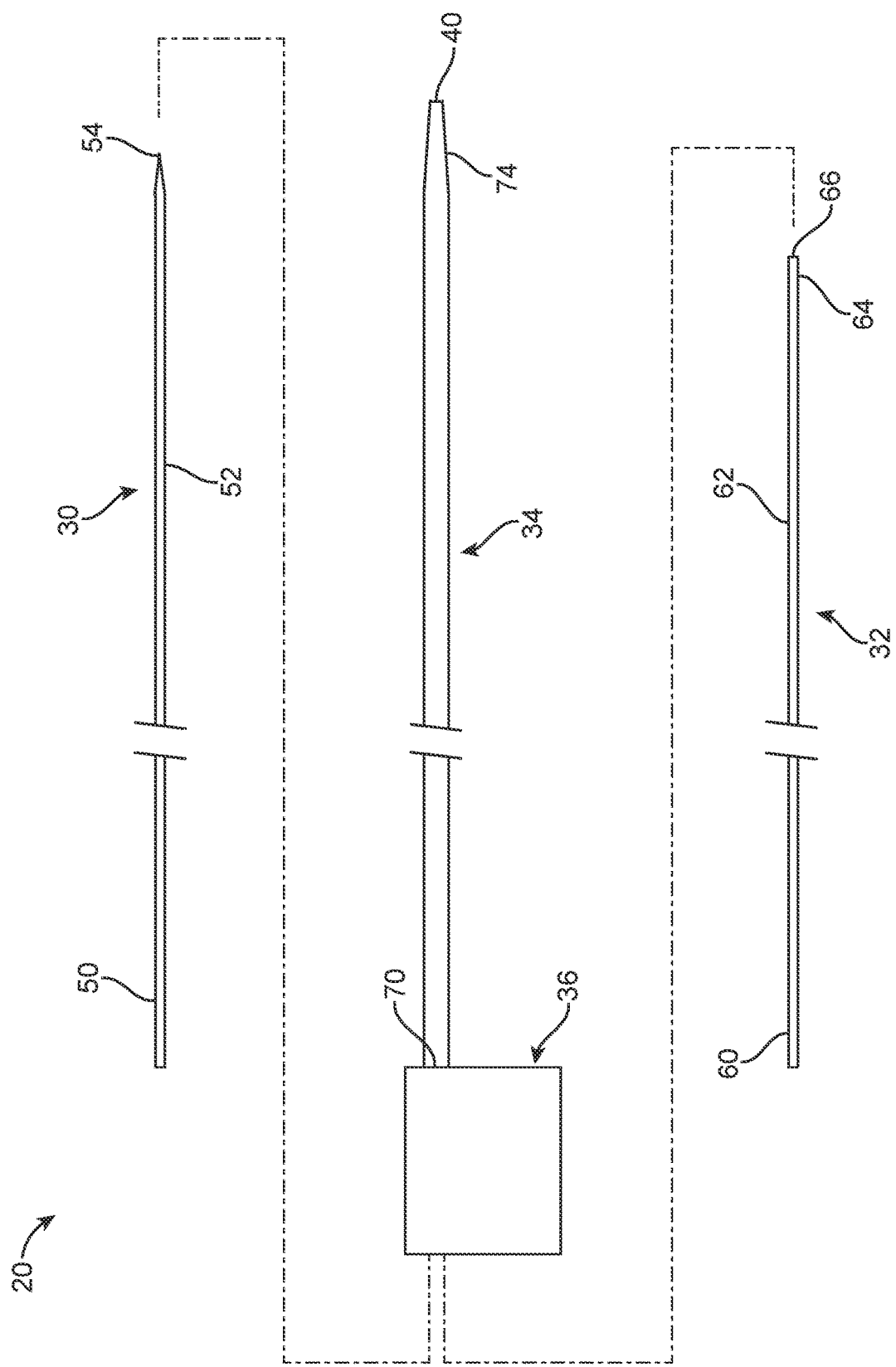
FIG. 1 is simplified, exploded view of a transseptal system in accordance with principles of the present disclosure.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Some aspects of the present disclosure provide a transseptal system for performing an intracardiac transseptal puncture and access procedure. One example of a transseptal system 20 in accordance with principles of the present disclosure is shown in simplified form in FIG. 1, and includes a needle body 30, a guidewire 32, a dilator body 34 and a handle 36. Details on the various components are provided below. In general terms, the dilator body 34 is connected to the handle 36, and terminates at distal end 40. Further, the dilator body 34 forms a lumen (not shown), a proximal region of which is sized to simultaneously receive the needle body 30 and the guidewire 32 via corresponding passages (not shown) in the handle 36. In a region of the distal end 40, the dilator body lumen is sized and shaped to slidably receive the needle body 30 or the guidewire 32 on an individual basis. With this construction, a transseptal puncture and access procedure can be performed, including puncturing tissue with the needle body 30 followed by immediate advancement of the guidewire 32 into the accessed area, eliminating the need for multiple instrument exchanges during the procedure.

The needle body 30 can assume various forms appropriate for performing a transseptal puncture as is known in the art (e.g., a Brockenbrough needle or similar tissue puncture device), and can be viewed as having or defining a proximal section 50, and intermediate section 52, and a distal tip 54. The intermediate section 52 is proximal the distal tip 54, and defines at least a majority of an axial length of the needle body 30. In this regard, the intermediate section 52 has a substantially uniform outer diameter (i.e., within 5% of a truly uniform outer diameter), with the diameter of the needle body 30 tapering to a sharped point along the distal tip 54. The proximal section 50 may or may not have an enlarged diameter as compared to the intermediate section 52. Further, the proximal section 50 may from or can be connected to an auxiliary component, such as a hub (not shown), for example a hub configured to facilitate flushing or pressure monitoring of an optional internal lumen of the needle body 30. In some embodiments, the needle body 30 is formed of metal or other electrically conductive material that can optionally allow for electrical ablation (e.g., via RF energy applied by the needle body) to effect, or assisting in effecting, a tissue puncture.

The guidewire 32 can also have any construction known in the art conducive to traversing a patient's vascular system, for example through the femoral vein to the superior vena cava (SVC). The guidewire 32 can be viewed as defining a proximal segment 60, an intermediate segment 62, and a leading segment 64 terminating at a leading end 66. The intermediate segment 62 defines at least a majority of an axial length of the guidewire 32, and has a substantially uniform outer diameter (i.e., within 5% of a truly uniform outer diameter). The leading segment 64 can have an outer diameter commensurate with that of the intermediate segment 60, or may exhibit a reduced outer diameter in extension to the leading end 66. In some embodiments, the leading segment 64 can be configured to self-assume a predetermined shape, such as a J-tip as is known in the art. With these and related embodiments, the leading segment 64 can be forced to a straightened shape (e.g., when disposed within a lumen of a separate device), and will self-revert to the predetermined shape when the force is removed (e.g., the guidewire 32 can be formed from a shape memory type material). The proximal segment 60 may or may not have an enlarged diameter as compared to the intermediate segment 62, and from or be connected to an auxiliary component, such as a handle (not shown).

The dilator body 34 can be, or can be akin to, an elongated sheath or tube, and defines a proximal end 70 opposite the distal end 40. At least a majority of the dilator body 34 can have a substantially uniform outer dimension or shape in longitudinal extension from the proximal end 70 to a distal zone 74. An outer dimension of the dilator body 34 can taper along the distal zone 74 to the distal end 40, with the distal zone 74 thus serving as an atraumatic surface for expanding a hole or opening in tissue when inserted there through as is known in the art. The dilator body 34 can be longitudinally straight or can be formed to define a curve along a longitudinal length thereof.

Figure 2:
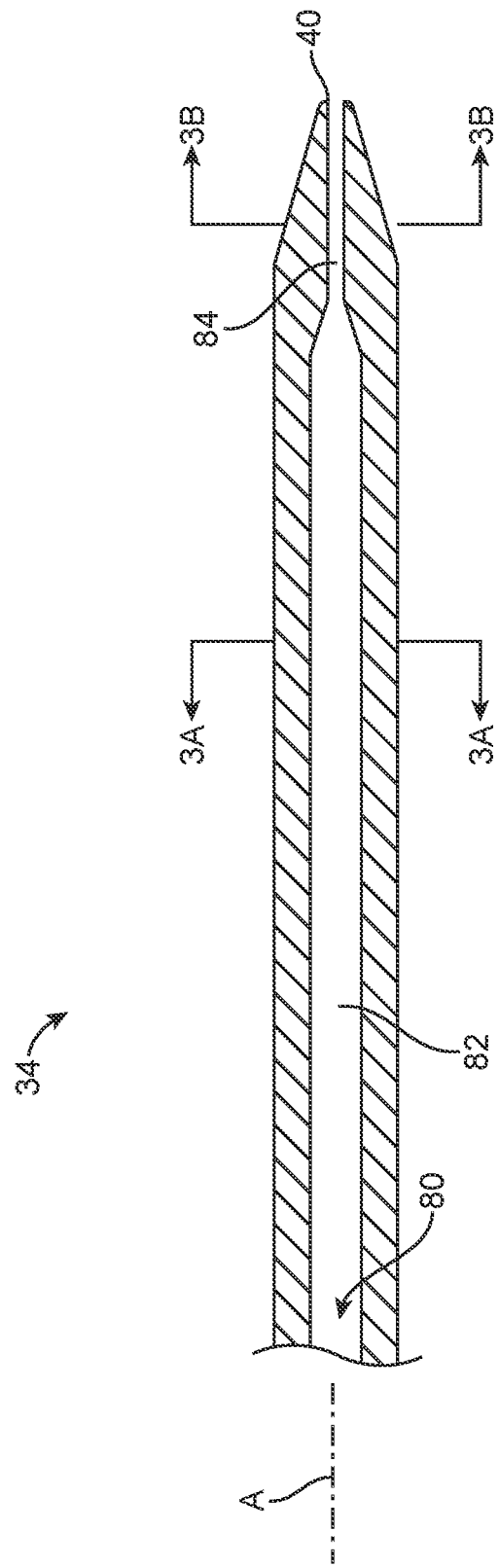
FIG. 2 is a simplified, longitudinal cross-sectional view of a portion of a dilator body component of the system of FIG. 1.

With additional reference to FIG. 2, the dilator body 34 defines a lumen 80 extending between the proximal end 70 and the distal end 40. A size and/or shape of the lumen 80 varies along a length of the dilator body 34, and can include a proximal region 82 and a distal region 84. The proximal region 82 of the lumen 80 is open to the proximal end 70, and the distal region 84 is open to the distal end 40. In general terms, the proximal region 82 of the lumen 80 is sized and/or shaped to simultaneously receive both the intermediate section 52 of the needle body 30 and the intermediate segment 62 of the guidewire 32, whereas the distal region 84 is sized and/or shaped to receive only one of the needle body 30 and the guidewire 32 on an individual basis.

Figure 3A:
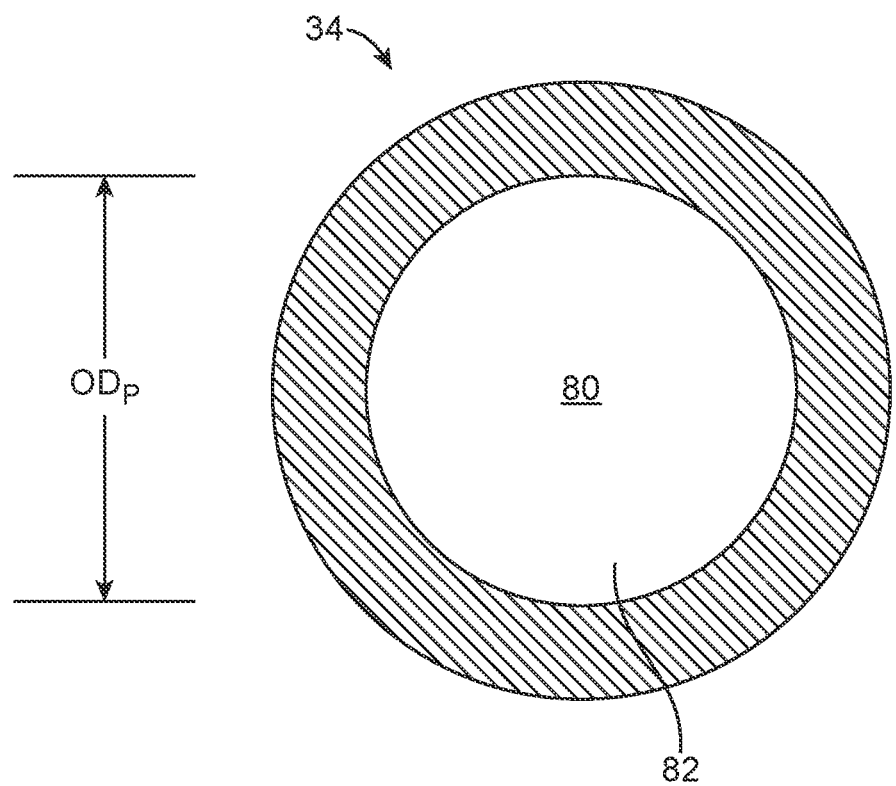
FIG. 3A is a transverse cross-sectional view of the dilator body of FIG. 2, taken along the line 3A-3A.
Figure 3B:
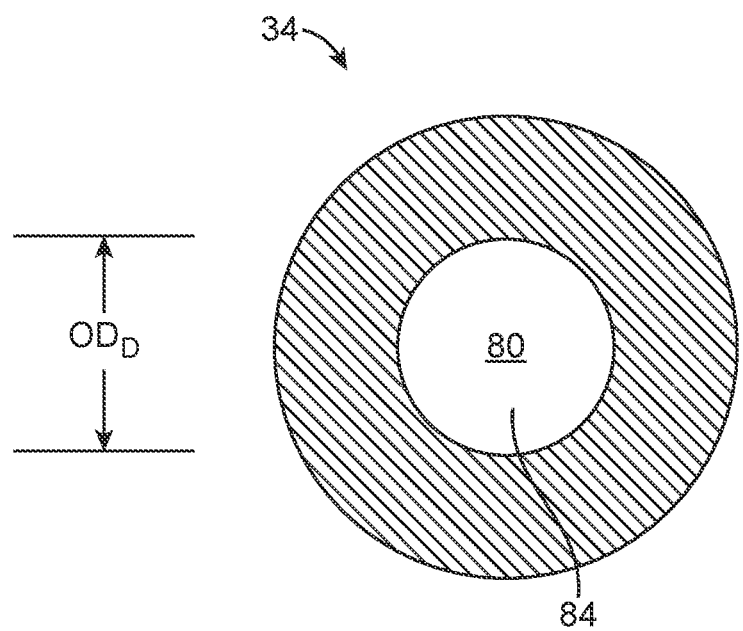
FIG. 3B is a transverse cross-sectional view of the dilator body of FIG. 2, taken along the line 3B-3B.

Geometry features of the lumen 80 in accordance with some embodiments of the present disclosure can be described with respect to a longitudinal axis A defined by the elongated shape of the dilator body 34. For example, FIG. 3A is a transverse cross-sectional representation of the dilator body 34 along the proximal region 82 of the lumen 80, taken in a plane perpendicular to the longitudinal axis A; FIG. 3B is a transverse cross-sectional representation along the distal region 84, also in a plane perpendicular to the longitudinal axis A. As a point of reference, while FIGS. 3A and 3B illustrate the lumen 80 as having a circular shape in transverse cross-section at both the proximal region 82 and the distal region 84, other shapes are also acceptable (regular shapes or irregular shapes), and the shape need not be the same or uniform at the proximal and distal regions 82, 84. Regardless, a shape of the lumen 80 defines a maximum outer dimension (e.g., a diameter in the non-limiting examples of FIGS. 3A and 3B). For example, the lumen 80 has a maximum outer dimension $OD_P$ along the proximal region 82 (again, in transverse cross-section), and a maximum outer dimension $OD_D$ along the distal region 84. The transverse cross-sectional maximum outer dimension $OD_P$ of the lumen 80 along the proximal region 82 is greater than the transverse cross-sectional maximum outer dimension $OD_D$ along the distal region 84. In some embodiments, a transverse cross-sectional area of the lumen 80 along the proximal region 82 is greater than a transverse cross-section area along the distal region 84. With additional reference to FIG. 2, a transition region 86 can be established between the proximal region 82 and the distal region 84 along with the lumen 80 tapers in outer dimension. Regardless, a longitudinal length of the distal region 84 is less than a longitudinal length of the proximal region 82, for example at least 75% less is some embodiments. In other embodiments, a longitudinal length of the distal region 84 (i.e., longitudinal distance from the distal end 40 to the transition region 86) can be on the order of 0.5-10 centimeters, alternatively not more than 5 centimeters. In some embodiments, the distal region 84 of the lumen 80 can generally correspond with a location of the distal zone 74.

Figure 4A:
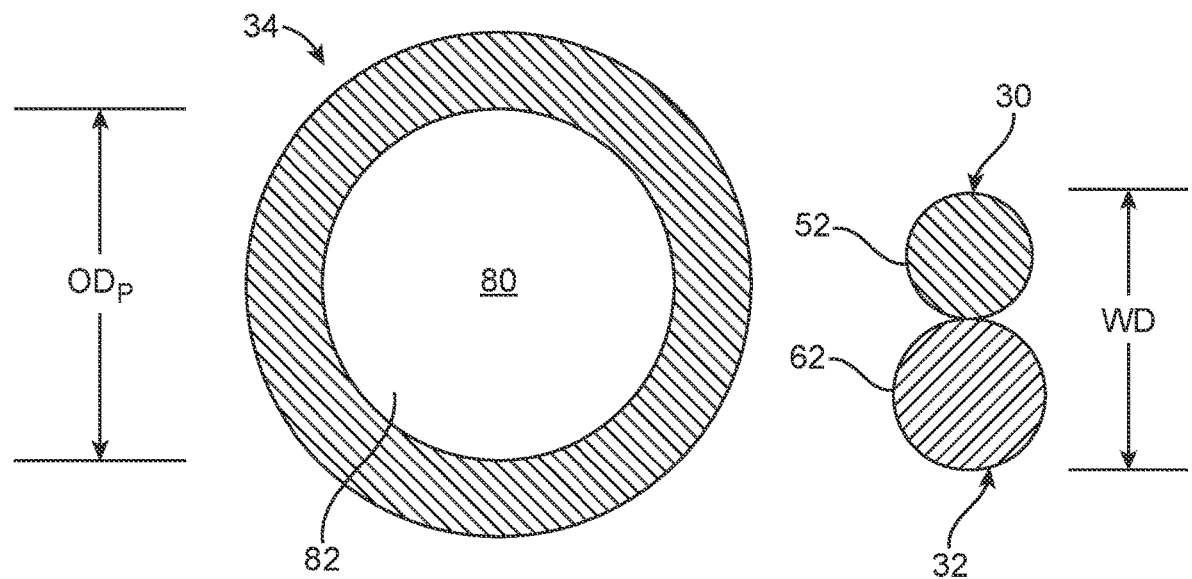
FIG. 4A is a transverse cross-sectional view of needle body and guidewire components of the system of FIG. 1, along with the dilator body cross-section of FIG. 2.
Figure 4B:
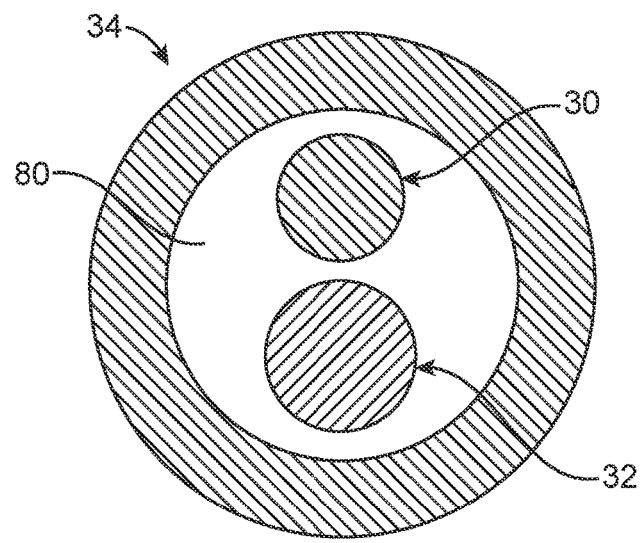
FIG. 4B is a transverse cross-sectional view representing the needle body and guidewire disposed within the dilator body.

As indicated above, a size and/or shape of the lumen 80 along each of the proximal and distal regions 82, 84 is selected in accordance with traverse cross-sectional geometry features of the needle body 30 and the guidewire 32. For example, FIG. 4A illustrates the transverse cross-sectional representation of the dilator body 34 along the proximal region 82 (as in FIG. 3A), along with side-by-side, transverse cross-sectional representations of the needle body 30 (along the intermediate section 52) and the guidewire 32 (along the intermediate segment 62). While the needle body intermediate section 52 and the guidewire intermediate segment 62 may or may not have the circular transverse cross-sectional shape implicated by FIG. 4A. Further, a transverse cross-sectional area of the needle body intermediate section 52 may or may not be less than a transverse cross-section area of the guidewire intermediate segment 62 as otherwise implicated by FIG. 4A. Regardless, when arranged side-by-side, the needle body intermediate section 52 and the guidewire intermediate segment 62 combine to define a maximum combined working dimension WD in transverse cross-section. With this in mind, the transverse cross-sectional maximum outer dimension $OD_P$ of the lumen 80 along the proximal region 82 is greater than the transverse cross-sectional maximum combined working dimension WD of the needle body intermediate section 52 and the guidewire intermediate segment 62. In other embodiments, a relationship of the proximal region 82 with respect to the needle body 30 and the guidewire 32 can be described as the transverse cross-sectional area of the lumen 80 along the proximal region 82 is greater than a combined transverse cross-sectional area of the needle body intermediate section 52 and the guidewire intermediate segment 62. With this construction, the needle body 30 (and in particular at least the intermediate section 52 thereof) and the guidewire 32 (and in particular at least the intermediate segment 62 thereof) can simultaneously reside within the lumen 80 along the proximal region 82 as reflected by FIG. 4B.

In contrast, and with reference between FIGS. 3B and 4A, the transverse cross-sectional maximum outer dimension $OD_D$ of the lumen 80 along the distal region 84 is less than the transverse cross-sectional maximum combined working dimension WD of the needle body intermediate section 52 and the guidewire intermediate segment 62. In other embodiments, a relationship of the distal region 84 with respect to the needle body 30 and the guidewire 32 can be described as the transverse cross-sectional area of the lumen 80 along the distal region 84 is less than a combined transverse cross-sectional area of the needle body intermediate section 52 and the guidewire intermediate segment 62. With this construction, the needle body intermediate section 52 and the guidewire intermediate segment 62 cannot simultaneously reside within the lumen 80 along the distal region 84 in some embodiments. However, the transverse cross-sectional maximum outer dimension $OD_D$ of the lumen 80 along the distal region 84 is at least slightly greater than the transverse cross-sectional maximum outer dimension of the needle body intermediate section 52, and is at least slightly greater than the transverse cross-sectional maximum outer dimension of the guidewire intermediate segment 62. In other embodiments, the transverse cross-sectional area of the lumen 80 along the distal region 84 is greater than the transverse cross-sectional area of the needle body intermediate section 52, and is greater than the transverse cross-sectional area of the guidewire intermediate segment 62. Thus, the needle body intermediate section 52 or the guidewire intermediate segment 62 can each be slidably received on an individual basis within the lumen 80 along the distal region 84, but not simultaneously.

Figure 5:
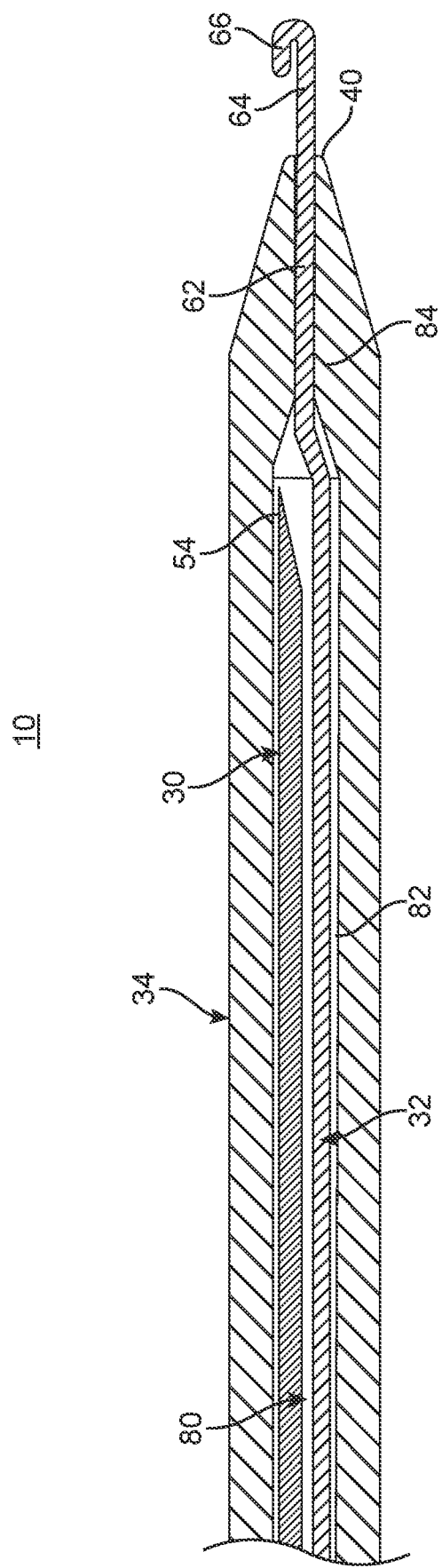
FIG. 5 is a simplified, longitudinal cross-sectional view of a portion of the system of FIG. 1, including the dilator body, needle body and guidewire.

Geometry features of the dilator body lumen 80 relative to the needle body 30 and the guidewire 32 can further be described with reference to FIG. 5. In the arrangement of FIG. 5, the needle body 30 and the guidewire 32 have been loaded into the lumen 80, and simultaneously reside along the proximal region 82. The needle body 30 is arranged such that the distal tip 54 is within the proximal region 82 of the lumen 80 (i.e., is proximal the distal end 40 of the dilator body 34), whereas the guidewire 32 has been distally advanced relative to the needle body 30 and the dilator body 34, including the intermediate segment 62 extending along and through the distal region 84 of the lumen 80, and the leading end 66 located distal the distal end 40 of the dilator body 34. As a point of reference, FIG. 5 further reflects an optional construction of the guidewire 32 in which the leading segment 64 self-reverts to a J-like shape when released from the confines of the lumen 80. Regardless, with the arrangement of FIG. 5, the distally exposed portion of the guidewire 32 can be utilized in performing one or more steps of an intended procedure, while the needle body 30 remains "covered" by the dilator body 34. In some embodiments, then, FIG. 5 represents a first deployment state of the transseptal system 10. When a particular procedure calls for deployment of the needle body 30, the guidewire 32 can be proximally retracted relative to the dilator body 34, bringing the leading end 66 into the proximal region 82 of the lumen 80 such that the guidewire 32 no longer occupies the distal region 84; the needle body 30 can then be distally advanced relative to the dilator body 34, directing the distal tip 54 into and through the distal region 84 of the lumen 80. In this second deployment state of the transseptal system 10, the distal tip 54 of the needle body 30 can be utilized for a desired procedural step (e.g., to pierce or puncture tissue), while the guidewire 32 remains "covered" by the dilator body 34. As desired, the needle body 30 can later be proximally retracted, followed by distal advancement of the guidewire 32. This instrument exchange (e.g., replacing the guidewire 32 with the needle body 30 distal the distal end 40 of the dilator body 34, or vice-versa) can be performed quickly, and does not necessitate complete removal of the needle body 30 or the guidewire 32 from the dilator body 34. Further, the needle body lumen 80 serves as a central lumen that is flushable.

Figure 6:
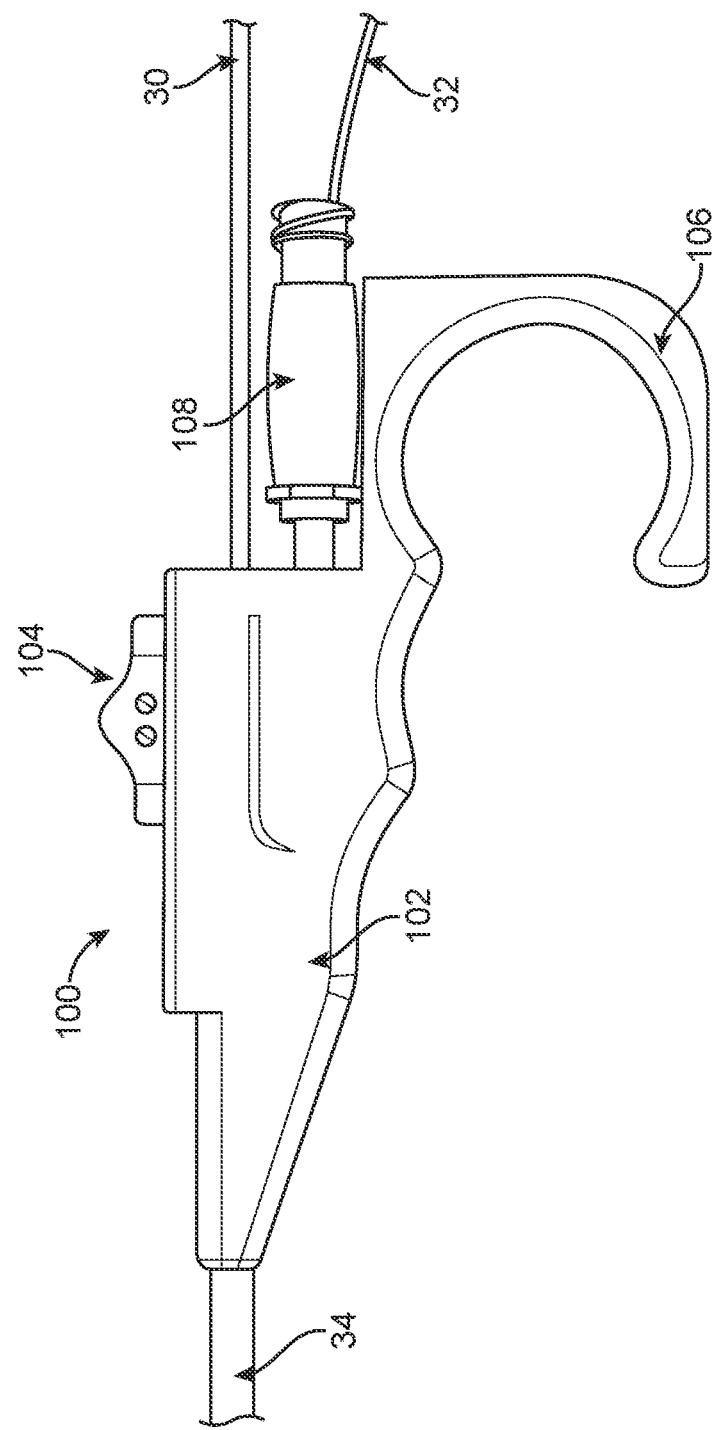
FIG. 6 is a side view of a portion of a transseptal system in accordance with principles of the present disclosure, including a handle assembly useful with the system of FIG. 1.

Returning to FIG. 1, the handle 36 can assume various forms conducive to loading and manipulating the needle body 30 and the guidewire 32 relative to the dilator body 34. In some embodiments, the proximal end 70 of the dilator body 34 can be attached (e.g., permanently attached such as be adhesive, welding, etc.) to the handle 36. In other embodiments, the dilator body 34 can be selectively mounted to the handle 36 by an end user. Further, the handle 36 can optionally be provided as part of a handle assembly having additional, optional features. With this in mind, one non-limiting example of a handle assembly 100 in accordance with principles of the present disclosure is shown in FIG. 6. The handle assembly 100 includes a handle 102, an optional actuator device 104 (referenced generally), an optional grip 106, and an optional connector hub 108. As a point of reference, in the view of FIG. 6, the dilator body 34 is fixed to the handle 102, and the needle body 30 and the guidewire 32 have been loaded to the handle 102. Where provided, the optional connector hub 108 is carried by the handle 102 and can have a conventional design appropriate for receiving the guidewire 32 (e.g., a Luer Lock-type connector hub).

In some embodiments, the handle 102 and the grip 106 can be integrally or homogenously formed, with the grip 106 generally configured to facilitate grasping of the handle assembly 100 by a single hand of a user. In some optional embodiments in which the dilator body 34 forms or defines a curve along a longitudinal length thereof, a shape or other feature of the grip 106 can be configured to indicate to a user a general direction of the curvature relative to the handle 102 (e.g., an indication as to which way the dilator body 34 is "pointing"). Alternatively or in addition, other features can be provided that denote orientation (e.g., a marking can be provided on the handle 102 to the effect of "curved dilator" or the like, indicating to a user which way the dilator body 34 is curved). Regardless, the grip 106 can assume various shapes and sizes that may or may not be implicated by the view of FIG. 6. In other embodiments, the grip 106 can be omitted. Regardless, and with reference to FIG. 7, the handle 102 defines, in some embodiments, a needle passage 120 and a guidewire passage 122. The needle passage 120 is sized to slidably receive at least the intermediate section 52 of the needle body 30 (FIG. 1), whereas the guidewire passage 122 is sized to slidably receive at least the intermediate segment 62 of the guidewire 32 (FIG. 1). Further, the needle passage 120 and the guidewire passage 122 are both open to a port 124 otherwise configured for connection to the dilator body 34 (FIG. 1). In particular, and as best shown in FIG. 8, upon assembly of the proximal end 70 of the dilator body 34 to the port 124, the lumen 80 is open to the needle passage 120 and the guidewire passage 122. Thus, the needle body 30 can extend through the needle passage 120 and the lumen 80, and the guidewire 32 can extend through the guidewire passage 122 and the lumen 80. As a point of reference, FIG. 8 generally reflects one non-limiting example of a connection between the dilator body 34 and the handle 102 in accordance with principles of the present disclosure in which the proximal end 70 is inserted into the port 124. In other embodiments, the proximal end 70 can be inserted over the port 124. With these and other techniques, the dilator body 34 can optionally be permanently affixed to the handle 102 (e.g., adhesive, welding, etc.). In other embodiments, a releasable connection can be established. In yet other embodiments, one or more additional structures or components can be provided that facilitate connection between the dilator body 34 and the handle 102. Regardless, upon final assembly, the dilator body lumen 80 is open to the needle passage 120 and the guidewire passage 122. In other embodiments of the present disclosure, the handle 102 forms a single passage open to the dilator body lumen 80 and sized to simultaneously receive both the needle body 30 and the guidewire 32.

Figure 7:
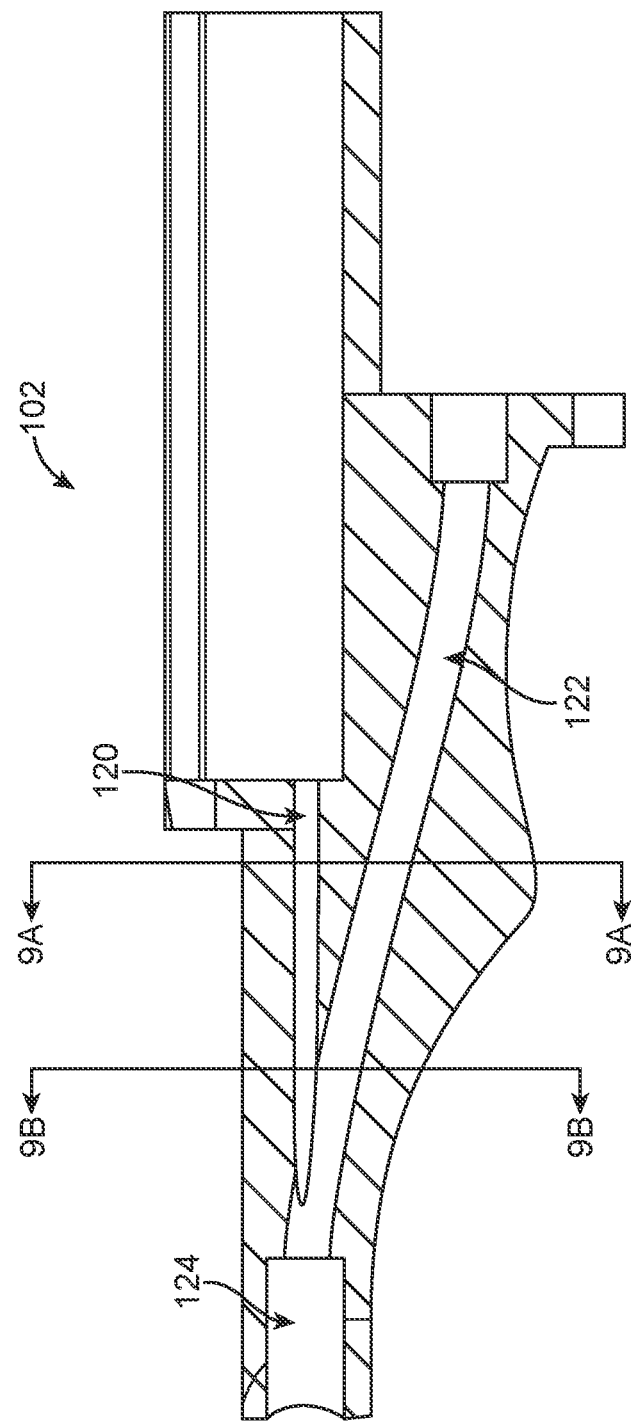
FIG. 7 is a longitudinal cross-sectional view of a handle component of the handle assembly of FIG. 6.
Figure 8:
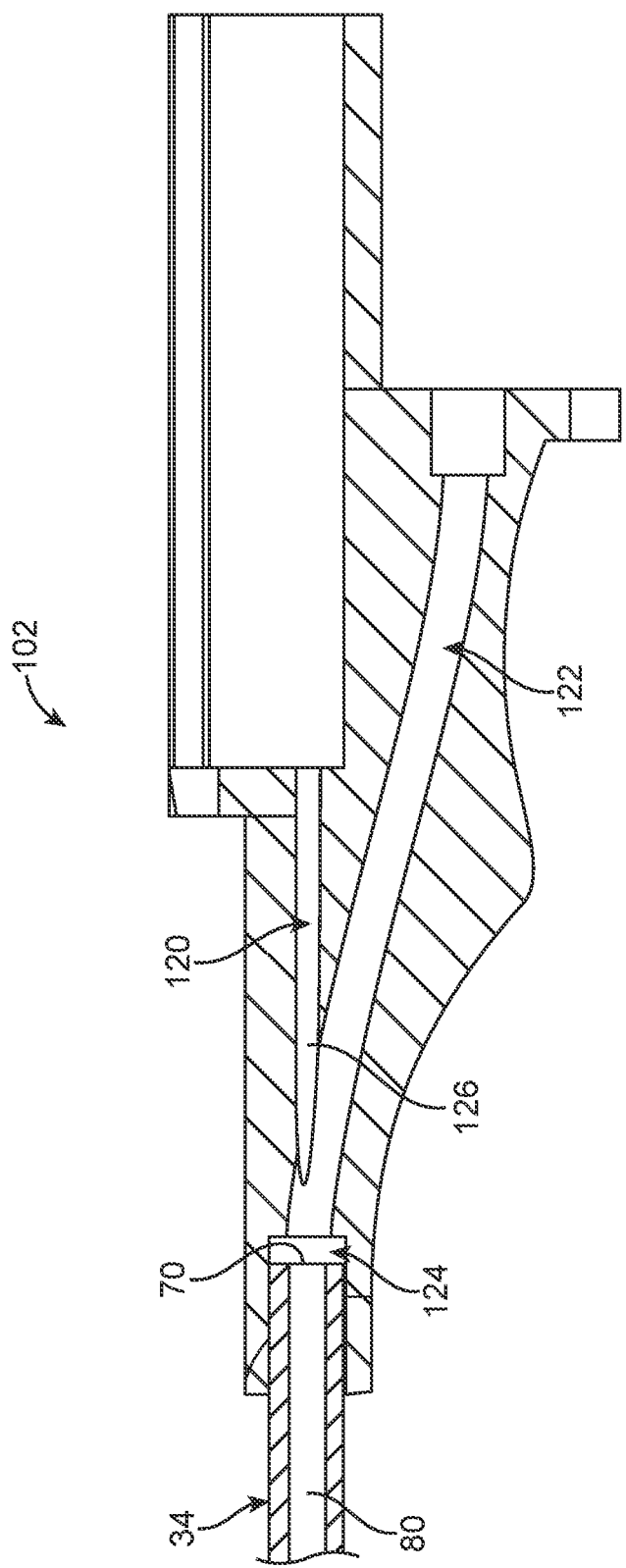
FIG. 8 is the cross-sectional view of the handle of FIG. 7, along with a portion of the dilator body assembled to the handle.
Figure 9A:
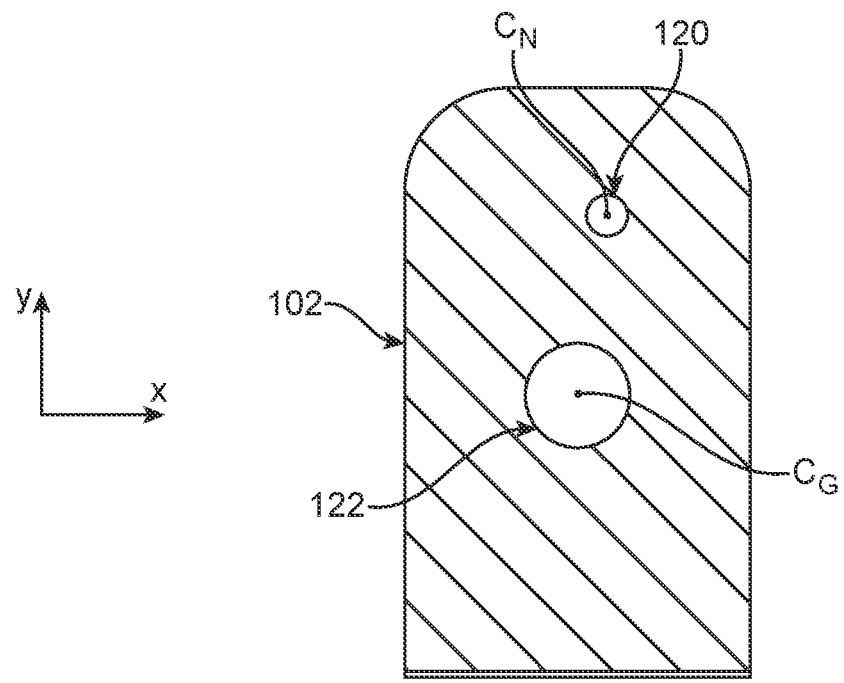
FIG. 9A is a transverse cross-sectional view of the handle of FIG. 7, taken along the line 9A-9A.
Figure 9B:
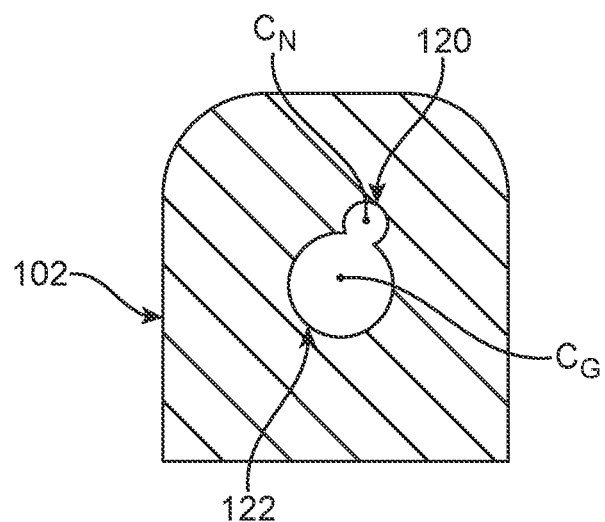
FIG. 9B is a transverse cross-sectional view of the handle of FIG. 7, taken along the line 9B-9B.

The handle 102 is shown in an upright orientation in the views of FIGS. 7 and 8, reflecting an orientation when handled by a user. Relative to this upright or "in use" orientation, the needle passage 120 can be arranged generally vertically above the guidewire passage 122 in some embodiments. Further, the passages 120, 122 can be arranged such that a distal side 126 of the needle passage 120 intersects the guidewire passage 122. In some embodiments, at least at the point of intersection of the needle passage 120 with the guidewire passage 122, a longitudinal centerline of the needle passage 120 is off-set from that of the guidewire passage 122. For example, the cross-section of FIG. 9A illustrates the needle passage 120 having or defining a longitudinal centerline $C_N$ and the guidewire passage 122 having or defining a longitudinal centerline CG. In the cross-sectional plane of FIG. 9A, while the needle passage 120 and the guidewire passage 122 are separate or distinct from one another, the needle passage centerline CN can be horizontally off-set (e.g., in the x-direction) from the guidewire passage centerline CP. In the cross-sectional plane of FIG. 9B, the needle passage 120 is now open to the guidewire passage 122. At this point of intersection, the needle passage centerline CN is off-set both horizontally and vertically relative to the relative to the guidewire passage centerline CG. With these and other off-set arrangements, a needle body extending through the needle passage 120 and into the guidewire passage 122 is less likely to interfere with a guidewire extending through the guidewire passage 122.

Figure 10:
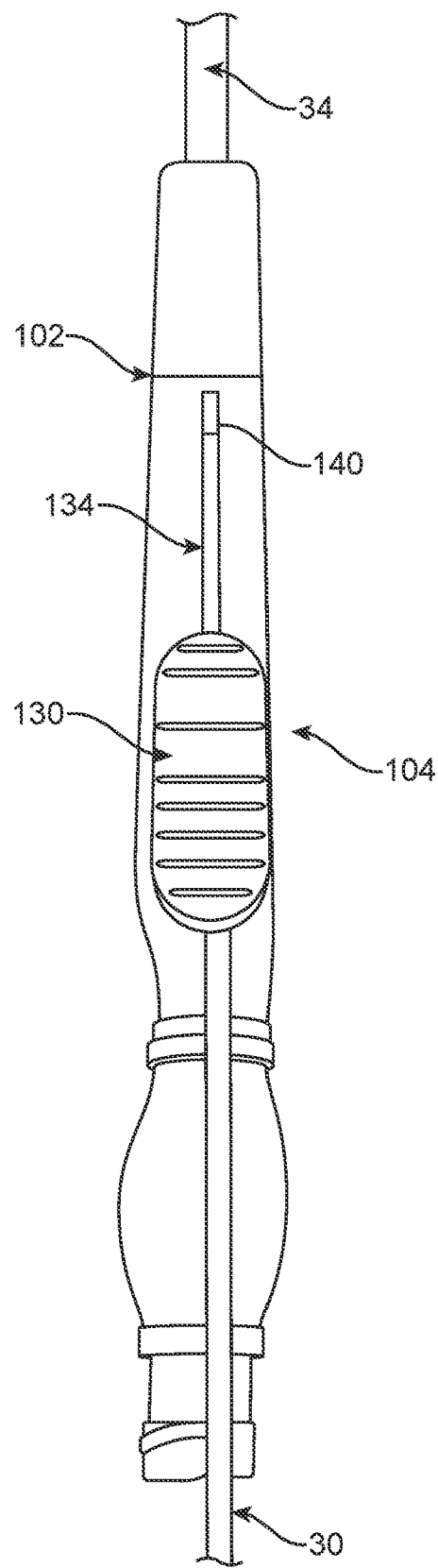
FIG. 10 is a top view of a portion of the system of FIG. 6.
Figure 11:
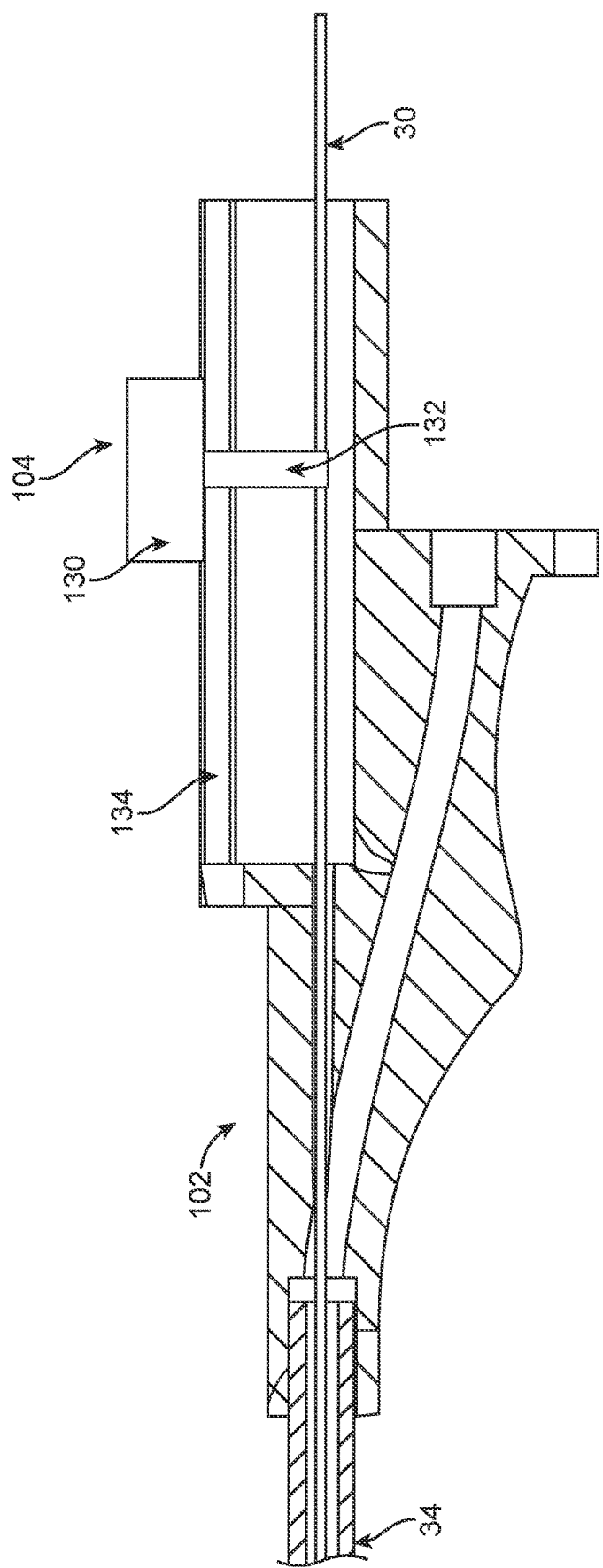
FIG. 11 is a longitudinal cross-sectional view of a portion of the system of FIG. 10.
Figure 12:
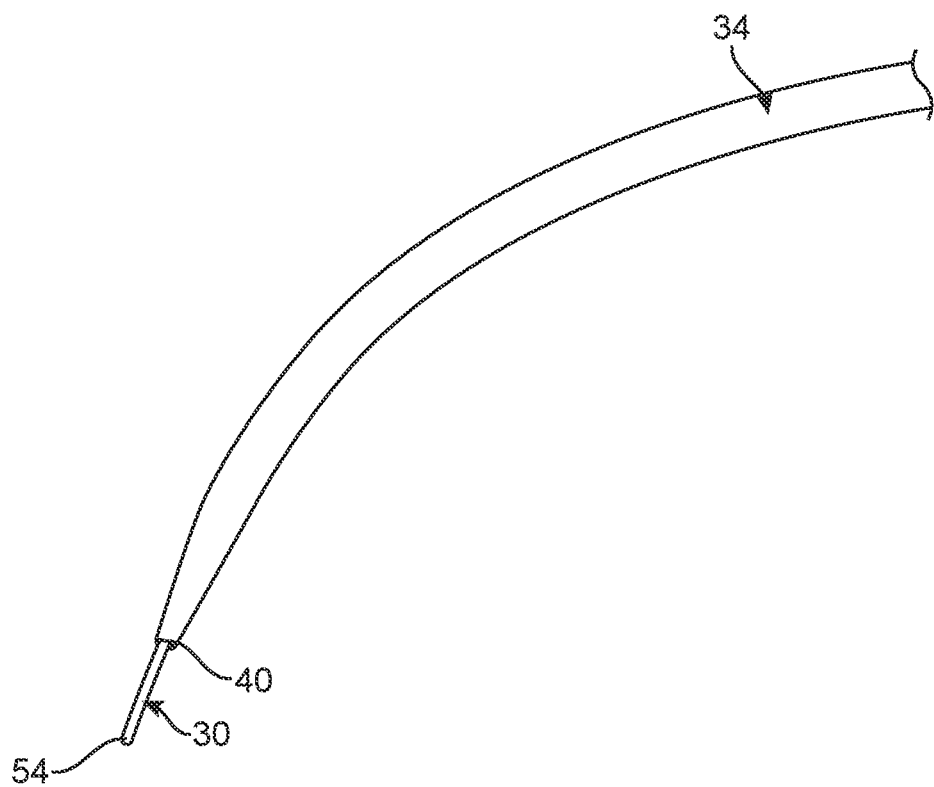
FIG. 12 is a side view of a portion of the system of FIG. 6, illustrating an arrangement of a needle distal tip relative to a dilator body distal end in a needle deployment state.

Returning to FIGS. 6 and 8, the handle assembly 100 can be configured to interface with the needle body 34 in various manners conducive to slidably maintaining the needle body 34 relative to the needle passage 120, and thus relative to the dilator body lumen 80. In some embodiments, the needle body 30 can be selectively assembled to and removed entirely from the handle assembly 100. In other embodiments, the handle assembly 100 is configured to retain the needle body 30 via the actuator device 104. For example, FIG. 10 is a top view of the handle assembly 100 with the needle body 30 and the dilator body 34 mounted thereto; FIG. 11 is a simplified cross-sectional view of the arrangement of FIG. 10. In some embodiments, the actuator device 104 is slidably connected to the handle 102, and includes a pusher body or head 130 and a neck 132. The neck 132 extends from the pusher body 130, and in configured to be affixed to the needle body 30 (e.g., adhesive, weld, etc.). The handle 102 defines a slot 134; the neck 132 is sized and shaped to be slidably received within the slot 134. In this regard, a width of the pusher body 130 is greater than that of the neck 132 and the slot 134 such that the pusher body 130 is slidable along an exterior of the handle 102. With this construction, then, the needle body 30 is slidably retained relative to the handle 102 (and thus relative to the dilator body 34) by the actuator device 104. In response to a user-applied force on the pusher body 130, the actuator device 104, and thus the needle body 30 attached thereto, can be manipulated relative to the handle 102 between a rearward position reflected in FIG. 10 and a forward position generally indicated at 140 in FIG. 10. A length of the needle body 30 between the point of attachment with the neck 132 and the distal tip 54 (FIG. 1) corresponds with a distance or length from the dilator body distal end 40 (FIG. 1) and the forward and rearward positions. In particular, when the actuator device 104 is in the rearward position, the needle body distal tip 54 is disposed within the proximal region 82 of the dilator body lumen 80 (e.g., the arrangement of the needle body distal tip 54 relative to the dilator body lumen 80 shown in FIG. 5). When the actuator device 104 is manipulated from the rearward position to the forward position 140, the needle body 34 is caused to slide distally relative to the dilator body 34, locating the needle body distal tip 54 distal the distal end 40 of the dilator body 34. In some embodiments, the handle assembly 100 is configured such that the pusher body 130 cannot be forced distally "beyond" the forward position 140 (e.g., a structure of the handle 102 serves as a hard stop to distal movement of the neck 132 beyond the distal end of the slot 134 that otherwise serves as the designated forward position); with these and related embodiments, the actuator device provides a predefined maximum distal extension of the needle body distal tip 54 relative to the dilator body distal end 40 such that the needle body distal tip 54 is not inadvertently caused to overly protrude relative to the dilator body distal end 40. FIG. 12 illustrates a relationship of the needle body distal tip 54 relative to the dilator body distal end 40 with the actuator device 104 (FIG. 11) in the forward position.

Figure 13A:
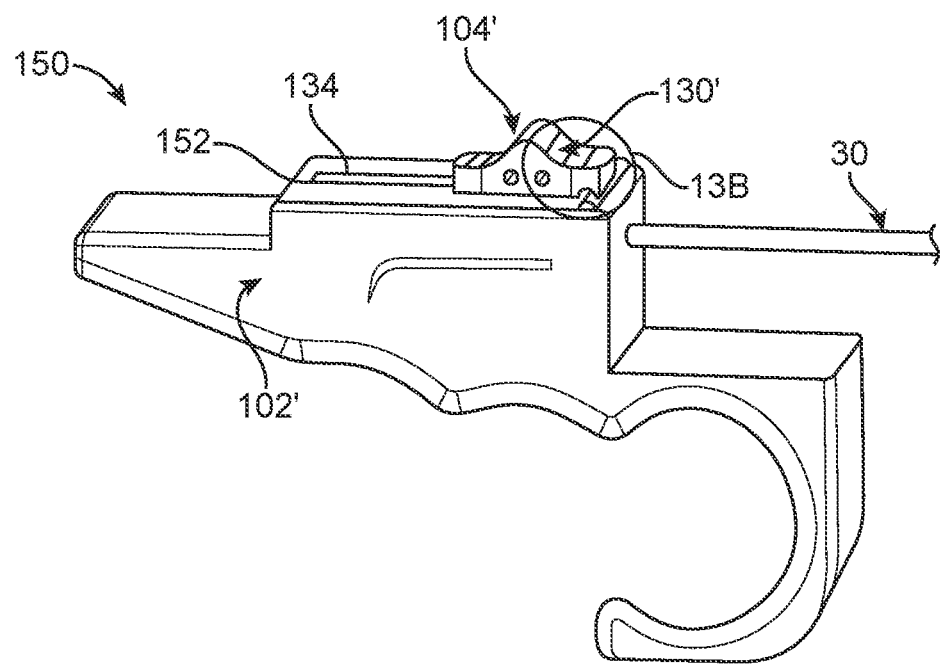
FIG. 13A is a simplified perspective view of a handle assembly useful with the system of FIG. 1, along with a needle body retained by the handle assembly.
Figure 13B:
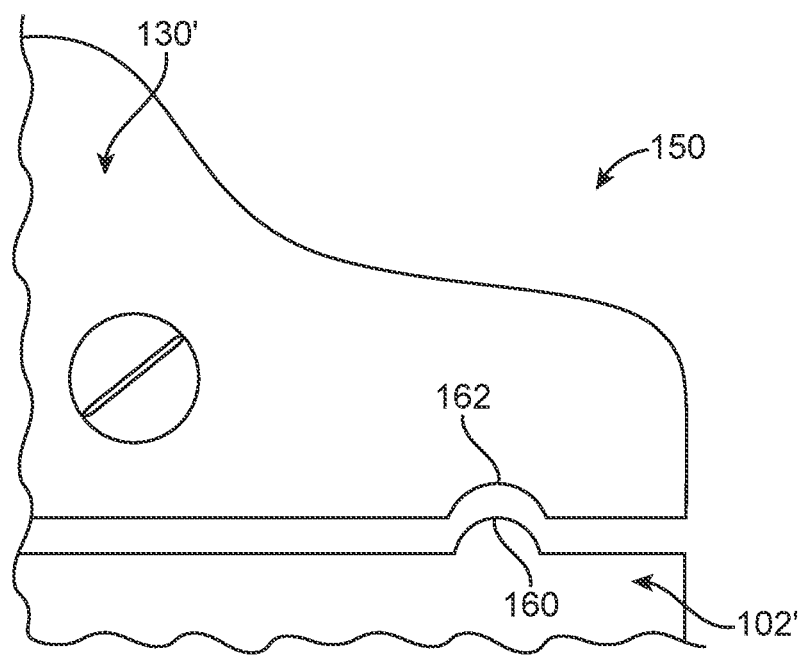
FIG. 13B is an enlarged side view of a portion of the handle assembly of FIG. 13A.

Returning to FIG. 6, the handle assembly 100 can incorporate or include one or more other components that facilitate a robust, slidable connection between the needle body 30 and the handle 102 that may or may not be implicated by the actuator device 104 as described above. In some embodiments, the handle assembly 100 can include or incorporate features that provide a user with visual and/or tactile cues as to a relationship of the needle body distal tip 54 relative to the dilator body distal end 40. For example, FIGS. 13A and 13B illustrate portions of an alternative handle assembly 150 in accordance with principles of the present disclosure and maintaining the needle body 30. The handle assembly 150 can be highly akin to the handle assembly 100 (FIG. 6), and includes a handle 102' and an actuator mechanism 104'. The handle 102' forms the slot 134 as described above and along which the actuator mechanism 104' is slidably retained. In this regard, the actuator mechanism 104' is coupled to the needle body 30 as described above, and includes a pusher body 130'. Commensurate with the descriptions above, the pusher body 130' is arranged to receive a user-applied actuation force, causing the pusher body 130' (and thus the needle body 30) to slide between a rearward position as shown, and a forward position (identified generally in FIG. 13A at 152). The handle 102' forms a protrusion or bump 160 proximate the slot 134 in a region corresponding to the rearward position, and the pusher body 130' forms a complementary groove or indent 162 sized to receive the bump 160. More particularly, the bump 160 and the indent 162 are configured and arranged such that when the pusher body 130' is in the rearward position, the bump 160 is captured within the indent 162, serving as a temporary "lock" of the actuator mechanism 104' (and thus of the needle body 30) relative to the handle 102'. It will be recalled that in the rearward position, the needle body distal tip 54 is disposed within the proximal region 82 of the dilator body lumen 80 (e.g., the arrangement of the needle body distal tip 54 relative to the dilator body lumen 80 shown in FIG. 5). Thus, the "lock" generated by an interface between the bump 160 and the indent 162 provides feedback to a user that the needle body distal tip 54 is "out of the way" or not otherwise exposed distal the dilator body 34. Further, the locked relationship between the bump 160 and the indent 162 resists accidental/unintentional movement of the actuator mechanism 104' relative to the handle 102', and thus of the needle body 30 relative to the dilator body 34. Instead, a user must make a concerted effort/apply a substantive pushing force onto the pusher body 130' in order to move the needle body 30 relative to the dilator body 34. Other complementary engagement arrangements configurations can be employed (e.g., the bump 160 can be carried by the pusher body 130') appropriate for providing a temporary lock; in yet other embodiments, the temporary locking features can be omitted.

Figure 14:
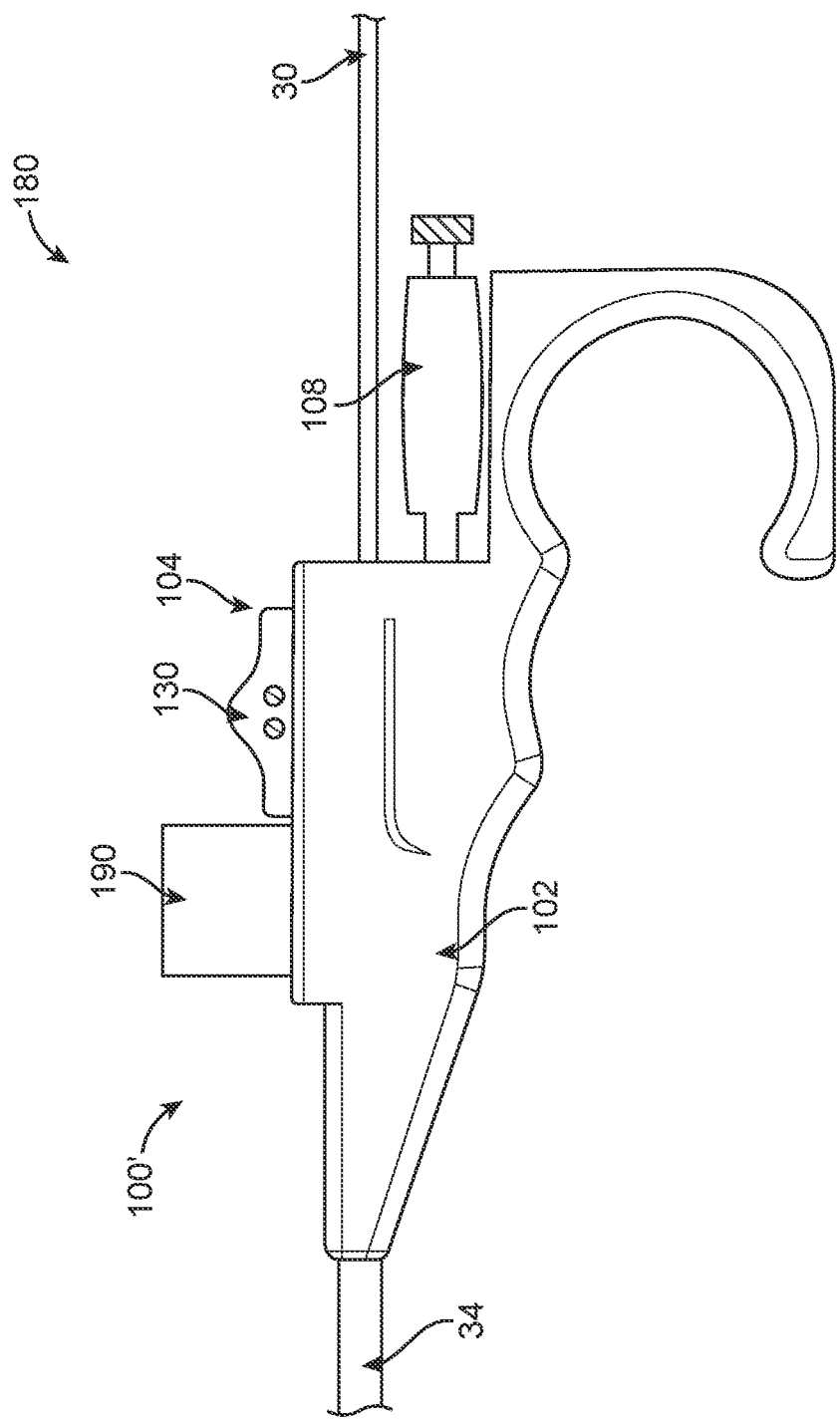
FIG. 14 is a simplified side view of a handle assembly useful with the system of FIG. 1, along with a needle body retained by the handle assembly.

Another optional feature that can be provided with some transseptal systems of the present disclosure is shown in FIG. 14. In particular, FIG. 14 illustrates, in simplified form, another transseptal system 180 in accordance with principles of the present disclosure that includes the needle body 30 and the dilator body 34 as described above, along with a handle assembly 100'. The handle assembly 100' can be highly akin to the handle assembly 100 (FIG. 6), and includes the handle 102, the actuator mechanism 104, and the optional guidewire connector hub 108. The handle assembly 100' further includes a safety tab 190 removably connected to the handle 102 (e.g., the safety tab 190 can have a "snap off" configuration whereby a user-applied force removes the safety tab 190 from the handle 102). As a point of reference, the arrangement of FIG. 14 represents one example of the system 180 as initially provided to a user. In this initial state, the actuator mechanism 104 secures the needle body 30 relative to the handle 102 (and thus relative to the dilator body 34), and is located in the rearward position. It will be recalled that in the rearward position, the needle body distal tip 54 is disposed within the needle body lumen 80 (i.e., the arrangement of FIG. 5). With this in mind, the safety tab 190 is configured and located along the handle 102 so as to inhibit forward or distal movement of the pusher body 130, thereby inhibiting unintentional or accidental forward or distal movement of the needle body distal tip 54 distally beyond the dilator body distal end 40. When deployment or extension of the needle body 30 is desired, the safety tab 190 is removed from the handle 102 by the user. Once removed, the pusher body 130 can then be freely manipulated by the user, for example to deploy or extend the needle body 30 from the dilator body 34.

Figure 15:
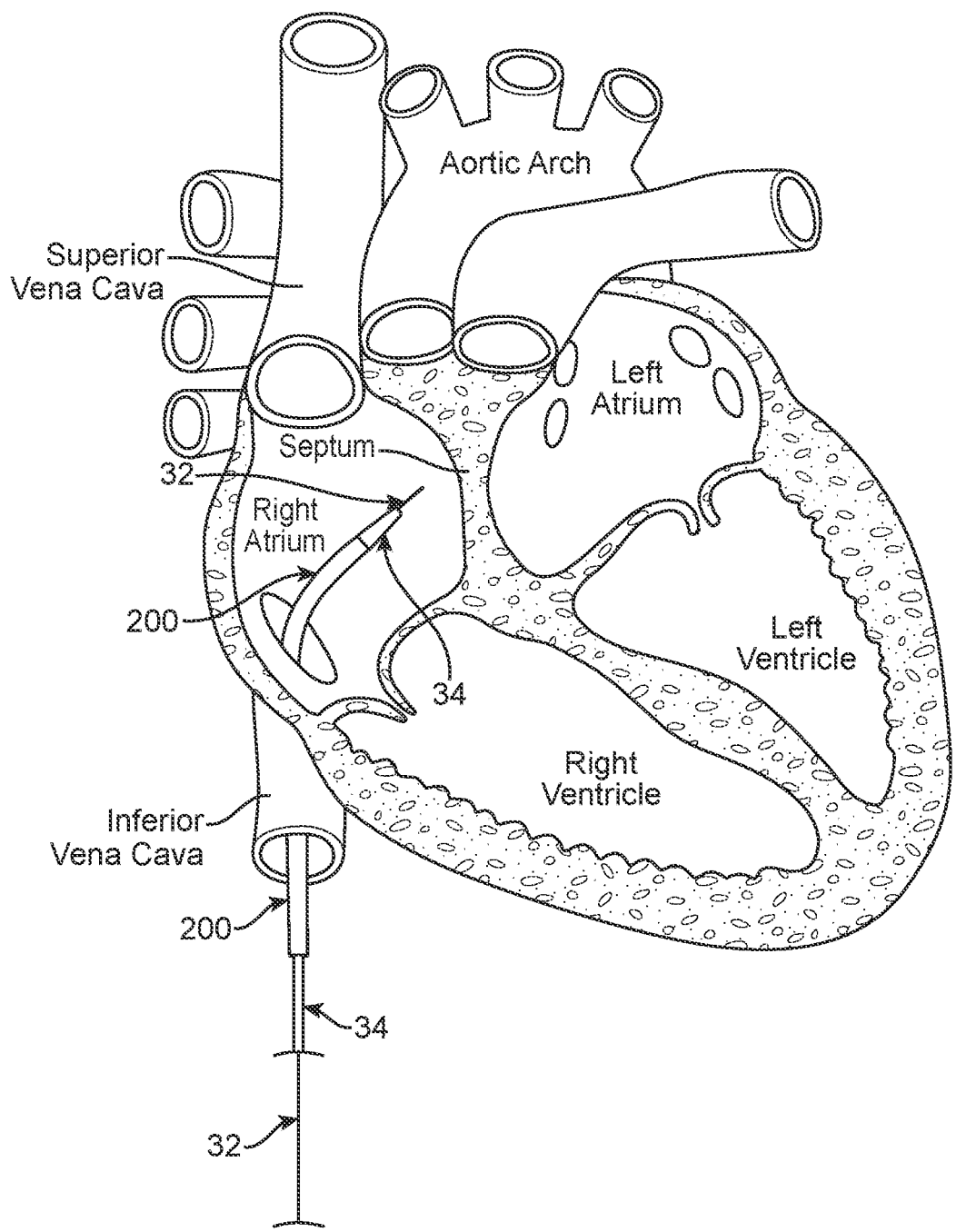
FIGS. 15-16C illustrate transseptal puncture and access methods in accordance with principles of the present disclosure.

The transseptal systems of the present disclosure can be useful in performing a variety of procedures requiring transseptal puncture and access. For example, any procedure that requires access to the left atrium via the interatrial septum, such as left ventricle endo pacing, left sided ablation, left atrial appendage closure, mitral valve repair/replacement, atrial septostomy, etc. Features of the present disclosure can be incorporated into any dilator designed to cross the septum. By way of non-limiting example, and with initial reference to FIG. 15, some methods of the present disclosure can include navigating the dilator body 34 to a patient's heart through the patient's vasculature, such as by femoral, radial, or brachial access. As a point of reference, some procedures requiring left atrial access necessitate the use of a delivery sheath 200 to deliver devices to their intended location within the left side of the heart or associated anatomies. The transseptal systems and methods of the present disclosure can be utilized in conjunction with such a delivery sheath to aid in navigation to atrial septal access point. The systems and methods of the present disclosure are in no way limited to use with a delivery sheath, and can include navigating the dilator body 34 with or without the delivery sheath 200. With this in mind, in the non-limiting example of FIG. 15, the delivery sheath 200 may be navigated from the femoral vein, through the inferior vena cava, and into the right atrium. With other techniques, the dilator body 34 is navigated into the right atrium via the radial, brachial, and superior vena cava. As reflected by FIG. 15, the guidewire 32 can be utilized to assist in locating the dilator body 34 and/or the optional delivery sheath 200 in the right atrium. It will be understood that at the procedural stage of FIG. 15, the needle body 30 is within the dilator body lumen 80 as the dilator body 34 is advanced to the right atrium (e.g., the arrangement of FIG. 5). From the right atrium, the transseptal systems of the present disclosure can be used to puncture the atrial septum, such as through the area of septal tissue known as the fossa ovalis, to gain access into the left atrium.

Figure 16A:
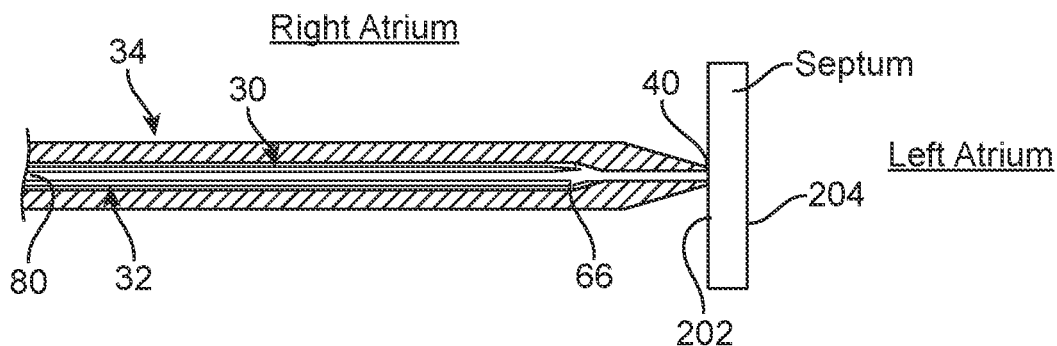
Figure 16B:
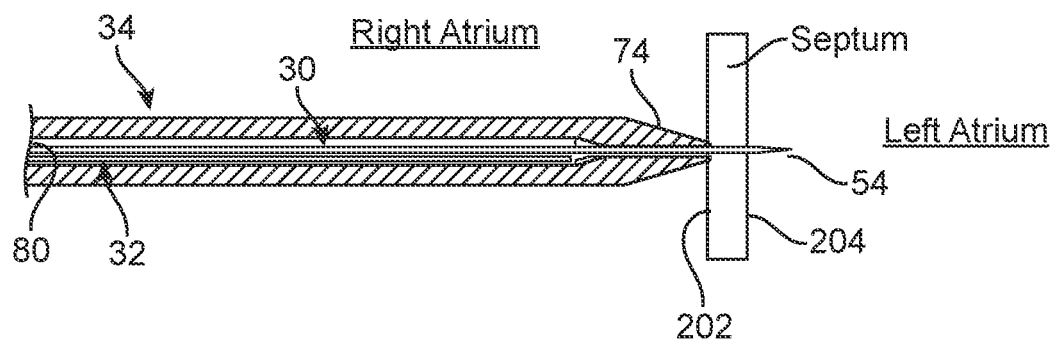

With reference to FIG. 16A, with the distal end 40 of the dilator body 34 proximate a first side 202 of the atrial septum, the guidewire 32 is retracted into the dilator body lumen 80 (i.e., the leading end 66 of the guidewire 32 is proximal the distal end 40 of the dilator body 34). As a point of reference, the optional delivery sheath 200 (FIG. 15) is omitted from the views of FIGS. 16A-16C for ease of understanding. Where the delivery sheath 200 is employed, the distal end 40 of the dilator body 34 can be distal a distal end of the delivery sheath 200 at the procedural stage of FIG. 16A. The dilator body 34 (and the needle body 30 contained therein) along with the optional delivery sheath 200 are manipulated (e.g., moved proximally and distally) until a desired location along the septum (e.g., the fossa ovalis) is located, for example using conventional techniques (e.g., ultrasound, fluoroscopy, etc.). The dilator body 34 and/or the delivery sheath 200 are then manipulated to push against and "tent" the first side 202 of the septum at the desired location in some embodiments. Regardless, the needle body 30 is then distally advanced relative to the dilator body 34, causing the distal tip 54 to puncture or pierce through a thickness of the septum as shown in FIG. 16B, creating a hole or access path in the septum (e.g., extending from the first side 202 to an opposing, second side 204 of the septum).

Figure 16C:
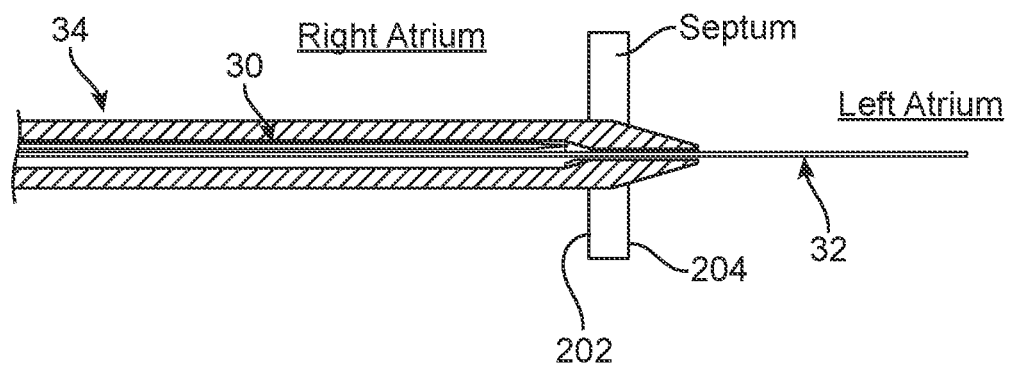

The puncture through the septum creates an access path from the right atrium to the left atrium. In some embodiments, the dilator body 34 and the needle body 30 are then advanced in tandem though the hole or access path in the septum and into the left atrium, with the dilator distal zone 74 enlarging the hole or access path. The needle body 30 is then retracted relative to the dilator body 34 (bringing the distal tip 54 within the dilator body lumen 80), followed by advancement of the guidewire 32 into the left atrium. In other embodiments, after puncturing the septum, the needle body 30 is first retracted relative to the dilator body 34 (bringing the distal tip 54 within the dilator body lumen 80); the guidewire 32 is then advanced into the left atrium, followed by advancement of the dilator body 34 over the guidewire 32 to enlarge the septal access path or opening with the dilator distal zone 74. Regardless, and as shown in FIG. 16C, the guidewire 32 is ultimately advanced distally beyond the second side 204 of the septum and into the left atrium while the needle body 30 remains within the dilator body lumen 80. Where desired, the dilator body 34 (and the needle body 30 contained therein) can be removed from the patient while the guidewire 32 remains in place, available for guiding other instruments to the left atrium. In yet other embodiments, the optional delivery sheath 200 can be advanced through the enlarged septal access path and into the left atrium, followed by removal of dilator body 34 (and the needle body 30 contained therein) and optionally the guidewire 32. With these and related embodiments, following removal of at least the needle body 30 and the dilator body 34, the delivery sheath 200 remains fully across the septum, available for guiding other instruments to the left atrium.

The systems and methods of the present disclosure provide a marked improvement over previous designs. The needle and guidewire are housed in a central lumen that is flushable. Following a septal puncture, the needle can be retracted, and the guidewire immediately advanced into the left atrium. This allows a user to advance a large sheath and dilator across the septum with a wire as a guide (sometimes referred to as rail support). Conventional systems and methods would necessitate that the needle be fully removed prior to the guidewire being introduced, so this step may at times be omitted. The systems and methods of the present disclosure can eliminate the need for needle exchanges prior to advancement of the guidewire. The systems and methods of the present disclosure can reduce complications during transseptal procedures, and can reduce the number of exchanges, which in turn can reduce the likelihood of possible harm. However, the systems and methods of the present disclosure may not dramatically alter the flow or feel associated with conventional transseptal crossing procedures.

Although the present disclosure has been described with reference to preferred embodiments, workers skilled in the art will recognize that changes can be made in form and detail without departing from the spirit and scope of the present disclosure

What is claimed is:

1. A transseptal system comprising:
   a needle body defining a distal tip and an intermediate section proximal the distal tip;
   a guidewire defining a leading end and an intermediate segment proximal the leading end;
   a handle defining a needle passage and a guidewire passage, wherein the needle passage is sized to slidably receive the intermediate section of the needle body, and further wherein the guidewire passage is sized to slidably receive the intermediate segment of the guidewire;
   a dilator body defining a distal end, a proximal end, and a lumen having a distal region open to the distal end and a proximal region open to the proximal end;
   wherein the proximal end of the dilator body is coupled to the handle such that the lumen is open to the needle passage and the guidewire passage;
   and further wherein the proximal region of the lumen is sized to simultaneously receive the intermediate section of the needle body and the intermediate segment of the guidewire;
   and even further wherein the distal region of the lumen is sized to slidably receive the intermediate section of the needle body and the intermediate segment of the guidewire on an individual basis.

2. The transseptal system of claim 1, wherein the dilator body defines a longitudinal axis, and further wherein a cross-sectional maximum outer dimension of the distal region of the lumen in a plane perpendicular to the longitudinal axis is less than a cross-sectional maximum outer dimension of the proximal region of the lumen in a plane perpendicular to the longitudinal axis.

3. The transseptal system of claim 1, wherein a diameter of the intermediate section of the needle body and a diameter of the intermediate segment of the guidewire combine to define a maximum combined working dimension, and further wherein the dilator body defines a longitudinal axis, and even further wherein a cross-sectional maximum outer dimension of the distal region of the lumen in a plane perpendicular to the longitudinal axis is less than the maximum combined working dimension.

4. The transseptal system of claim 3, wherein a cross-sectional maximum outer dimension of the proximal region of the lumen is greater than the maximum combined working dimension.

5. The transseptal system of claim 1, wherein the transseptal system is configured to provide a first deployment state including:
   the intermediate section of the needle body disposed within the lumen;
   the distal tip of the needle body projecting beyond distal end of the dilator body; and
   the leading end of the guidewire disposed within the proximal region of the lumen.

6. The transseptal system of claim 5, wherein the transseptal system is configured to provide a second deployment state including:
   the intermediate segment of the guidewire disposed within the lumen;
   the leading end of the guidewire projecting beyond distal end of the dilator body; and
   the distal tip of the needle body disposed within the proximal region of the lumen.

7. The transseptal system of claim 1, wherein the needle passage extends from a proximal side to a distal side, the distal side intersecting, and open to, the guidewire passage.

8. The transseptal system of claim 1, wherein the handle is provided as part of a handle assembly further including an actuator device connected to the handle and configured to retain the needle body.

9. The transseptal system of claim 8, wherein the actuator device is slidably connected to the handle.

10. The transseptal system of claim 9, wherein the actuator device includes a pusher body and a neck, and further wherein the head extends from the pusher body and is affixed to the needle body.

11. The transseptal system of claim 10, wherein the pusher body is slidable relative to the handle between a forward position and a rearward position, and further wherein the transseptal system is configured such that in the forward position, the distal tip of the needle body is distal the distal end of the dilator body, and in the rearward position, the distal tip of the needle body is disposed within the proximal region of the lumen.

12. The transseptal system of claim 11, wherein the handle assembly further includes a safety tab removably connected to the handle and arranged to prevent the pusher body from being directed to the forward position.

13. A transseptal system comprising:
- a handle assembly including a handle defining a needle passage and a guidewire passage;
- a dilator body defining a longitudinal axis, distal end, a proximal end, and a lumen having a distal region open to the distal end and a proximal region open to the proximal end, wherein a cross-sectional maximum outer dimension of the distal region of the lumen in a plane perpendicular to the longitudinal axis is less than a cross-sectional maximum outer dimension of the proximal region of the lumen in a plane perpendicular to the longitudinal axis;
- wherein the proximal end of the dilator body is coupled to the handle such that the lumen is open to the needle passage and the guidewire passage; and
- a needle body coupled to the handle assembly and slidably received within the needle passage and the lumen.

14. The transseptal system of claim 13, further comprising a guidewire configured to be slidably received within the guidewire passage and the lumen.

15. A method of creating a transseptal passage, the method comprising:
- advancing a dilator body over a guidewire to bring a distal end of the dilator body into contact with a first side of an atrial septum, the guidewire being slidably received within a lumen of the dilator body;
- retracting the guidewire relative to the dilator body such that a leading end of the guidewire is located within the lumen;
- forming a hole through the septum with a needle body while the leading end of the guidewire is maintained within lumen, including advancing the needle body along the lumen to cause a distal tip of the needle body to extend from the distal end of the dilator body and puncture through the first side of the atrial septum to an opposing, second side of the atrial septum;
- retracting the needle body relative to the dilator body following the step of forming a hole such that the distal tip of the needle body is located within the lumen; and
- advancing the guidewire relative to the dilator body such that the leading end of the guidewire extends distally beyond the distal end of the dilator body and the second side of the atrial septum.

16. The method of claim 15, wherein during the step of advancing the dilator body over the guidewire, the distal tip of the needle body is located within the lumen.

17. The method of claim 15, wherein during the step of retracting the guidewire relative to the dilator body, the distal tip of the needle body is located within the lumen.

18. The method of claim 15, further comprising:
- advancing a distal zone of the dilator body through the hole to dilate the hole following the step of advancing the needle body.

19. The method of claim 18, further comprising:
- withdrawing the dilator body and the needle body from the patient following the step of advancing the distal zone of the dilator body through the puncture hole;
- wherein during the step of withdrawing, the guidewire remains within the patient and the leading end is located distally beyond the second side of the atrial septum.

20. The method of claim 19, further comprising:
- advancing a treatment device over the guidewire following the step of withdrawing the dilator body and the needle body.

* * * * *